United States Patent
Martini et al.

(10) Patent No.: US 9,505,162 B2
(45) Date of Patent: *Nov. 29, 2016

(54) APPARATUS FOR SHAPING PLASTIC PREFORMS, COMPRISING A STERILE CHAMBER

(71) Applicant: KRONES AG, Neutraubling (DE)

(72) Inventors: Oliver Martini, Honolfingen (CH); Michael Dahmen, Hamburg (DE); Patrick Engelhard, Elsendorf (DE)

(73) Assignee: Krones, AG, Neutraubling (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/620,269

(22) Filed: Feb. 12, 2015

(65) Prior Publication Data

US 2015/0217499 A1 Aug. 6, 2015

Related U.S. Application Data

(62) Division of application No. 13/056,976, filed as application No. PCT/EP2009/059922 on Jul. 31, 2009, now Pat. No. 8,985,990.

(30) Foreign Application Priority Data

Aug. 18, 2008 (DE) ........................ 10 2008 038 141

(51) Int. Cl.
*B29C 49/36* (2006.01)
*B29C 49/42* (2006.01)
(Continued)

(52) U.S. Cl.
CPC ........... *B29C 49/36* (2013.01); *B29C 49/4205* (2013.01); *B29C 49/46* (2013.01); *B29C 49/6409* (2013.01); *A61L 2202/23* (2013.01);
(Continued)

(58) Field of Classification Search
None
See application file for complete search history.

(56) References Cited

U.S. PATENT DOCUMENTS 2,659,655 A 11/1953 Sweet
4,063,867 A 12/1977 Janniere
(Continued)

FOREIGN PATENT DOCUMENTS

CN 102112287 6/2011
DE 1561985 5/1970
(Continued)

OTHER PUBLICATIONS

Document in Connection with Opposition Proceedings in Related European Patent No. 2319678 against Krones AG; Dated Mar. 25, 2013—European Parliament, Councel, Regulation (EC) No. 852/2004 of the European Parliament and Councel of Apr. 29, 2004.

(Continued)

*Primary Examiner* — Benjamin Schiffman
(74) *Attorney, Agent, or Firm* — Onello & Mello, LLP.

(57) ABSTRACT

An apparatus (1) for shaping plastic preforms (10) into plastic containers (2) is disclosed. Said apparatus (1) comprises a conveying device (2) on which a plurality of blowing stations (8) are arranged. Each of said blowing stations (8) encompasses a blow mold, within which a plastic preform (10) can be shaped into a plastic container (20). The apparatus (1) further comprises a clean chamber (6), within which the plastic preforms (10) can be conveyed. According to the invention, the zone of the conveying device (2) in which the blowing stations are arranged is located in the clean chamber (6), and at least one additional zone of the conveying device (2) is located outside the clean chamber (6).

14 Claims, 1 Drawing Sheet

(51) Int. Cl.
  *B29C 49/64* (2006.01)
  *B29C 49/06* (2006.01)
  *B29C 49/12* (2006.01)
  *B29C 49/46* (2006.01)
  *B65G 47/84* (2006.01)
  *B67C 3/22* (2006.01)
  *B29L 31/00* (2006.01)

(52) U.S. Cl.
  CPC .............. *B29C 49/06* (2013.01); *B29C 49/12* (2013.01); *B29C 2049/4697* (2013.01); *B29C 2791/005* (2013.01); *B29L 2031/712* (2013.01); *B65G 47/846* (2013.01); *B67C 2003/227* (2013.01)

(56) References Cited

U.S. PATENT DOCUMENTS

| | | |
|---|---|---|
| 4,590,734 A | 5/1986 | Ueda |
| 4,880,581 A | 11/1989 | Dastoli et al. |
| 5,671,591 A | 9/1997 | Fleenor |
| 6,026,867 A | 2/2000 | Klarl |
| 6,152,723 A | 11/2000 | Winter et al. |
| 6,185,910 B1 | 2/2001 | Achhammer |
| 6,830,084 B1 | 12/2004 | Friede |
| 7,165,582 B2 | 1/2007 | Till |
| 7,341,079 B2 | 3/2008 | Zanga |
| 7,396,225 B2 | 7/2008 | Hansen |
| 8,092,757 B2 | 1/2012 | Adriansens et al. |
| 2004/0231748 A1 | 11/2004 | Friede |
| 2005/0016624 A1 | 1/2005 | Till |
| 2005/0220927 A1 | 10/2005 | Hansen |
| 2006/0059862 A1 | 3/2006 | Zanga |
| 2006/0185321 A1 | 8/2006 | Raynaud |
| 2008/0277840 A1 | 11/2008 | Yanagimachi et al. |
| 2010/0047120 A1 | 2/2010 | Adriansens et al. |
| 2010/0199604 A1 | 8/2010 | Fischer |
| 2011/0133369 A1 | 6/2011 | Martini et al. |

FOREIGN PATENT DOCUMENTS

| | | |
|---|---|---|
| DE | 19731796 | 1/1999 |
| DE | 10145803 | 4/2003 |
| DE | 10213343 | 10/2003 |
| DE | 10326618 | 1/2005 |
| DE | 2006053193 | 5/2008 |
| EP | 0741080 | 11/1996 |
| EP | 0893396 | 1/1999 |
| EP | 1122168 | 8/2001 |
| EP | 1262447 | 12/2002 |
| EP | 1357081 | 10/2003 |
| JP | H04147824 | 5/1992 |
| WO | 9618541 | 6/1996 |
| WO | 9835815 | 8/1998 |
| WO | 0078664 | 12/2000 |
| WO | 2004065283 | 8/2004 |
| WO | 2004103817 | 12/2004 |
| WO | 2006136499 | 12/2006 |

OTHER PUBLICATIONS

Document in Connection with Opposition Proceedings in Related European Patent No. 2319678 against Krones AG; Dated Mar. 25, 2013—Thomson, Gale, "All in One" Plastics and Rubber Asia, Mar. 2003.

International Search Report dated Sep. 14, 2009 issued in corresponding application PCT/EP2009/059922.

Opponent Statement in Connection with Opposition Proceedings in Related European Patent No. 2319678 against Konsnes AG; Dated Jun. 18, 2014.

Document in Connection with Opposition Proceedings in Related European Patent No. 2319678 against Krones AG; Dated Mar. 25, 2013.

"Apparatus for Shaping Plastic Preforms, Comprising a Sterile Chamber" Specification, Drawings, Claims and Prosecution History, of U.S. Appl. No. 13/056,976, filed Jan. 31, 2011, by Oliver Matini.

Chinese Office Action dated Jan. 30, 2015 issued in corresponding application No. 2013102392277.

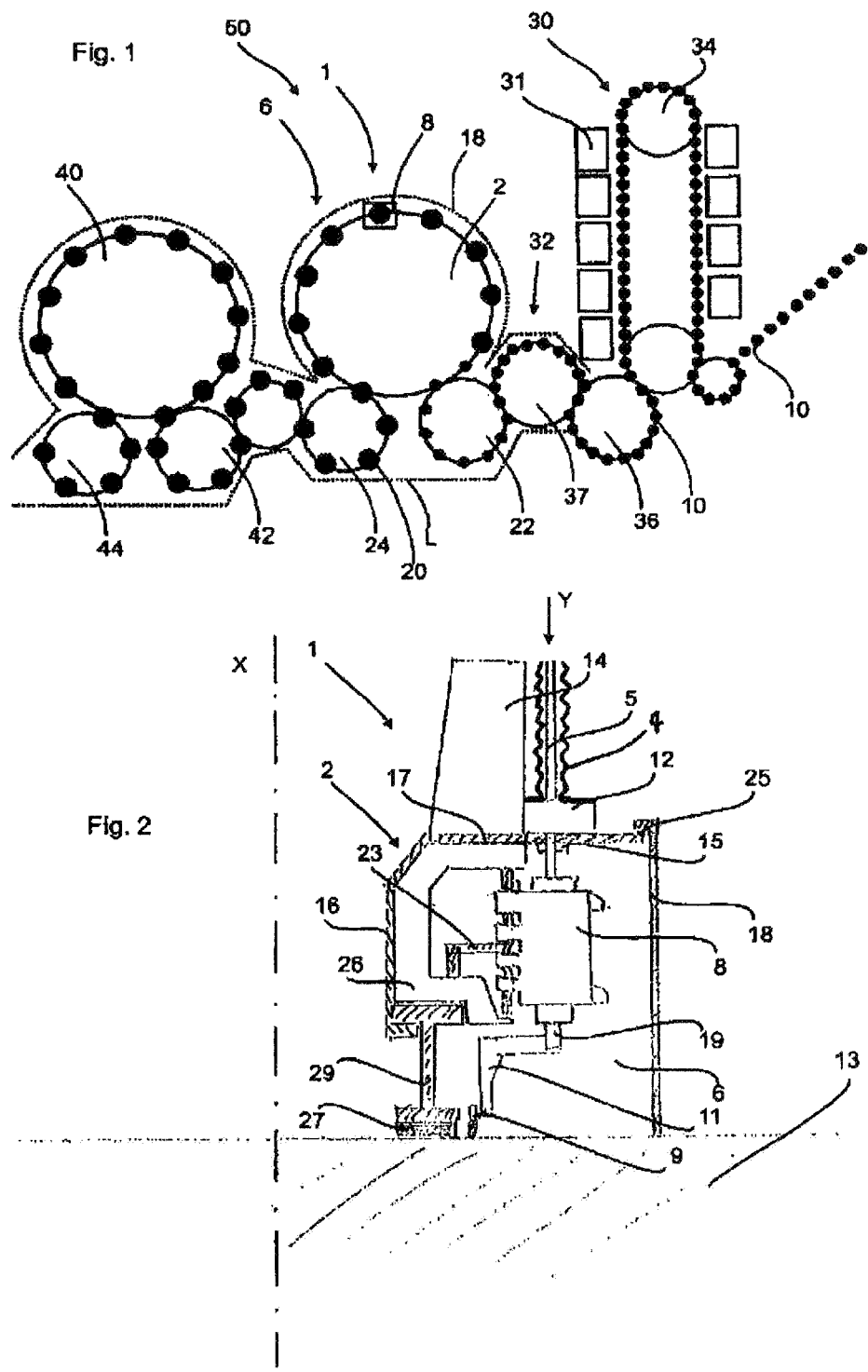

APPARATUS FOR SHAPING PLASTIC PREFORMS, COMPRISING A STERILE CHAMBER

The present invention relates to an apparatus for shaping plastics-material containers.

In the field of the beverage-producing industry it is known to use plastics-material containers, these plastics-material containers being produced from plastics-material pre-forms by a shaping procedure, and in particular a blow-moulding procedure. In this case it is customary to provide blow-moulding wheels on which a plurality of blow-moulding stations are arranged, the plastics-material pre-forms being expanded against an inner wall of the corresponding blow mould by being acted upon with compressed air inside these blow-moulding stations.

For many beverages it is necessary in this case for them to be filled under aseptic conditions. In this case it is known that a sterilization process for the aseptic filling begins with the sterilization of the already finished bottles in a clean room provided for this. All the processes taking place beforehand in the prior art, such as the production of the pre-forms, the transportation, the heating and the blow-moulding thereof to form bottles, take place in a non-sterile environment. In this case it is necessary for a relatively large area, namely that of the finished plastics-material bottle, to be sterilized.

It is therefore generally desirable to sterilize, not the plastics-material bottle itself, but rather the plastics-material pre-form, since the latter has a considerably smaller surface. Nevertheless, it is necessary for the containers to be conveyed under sterile conditions after the sterilization thereof, in particular in a continuous manner, at least until they are closed, in order to prevent in this way a further contamination of the containers.

EP 0 794 903 B1 describes a system and a method for the sterile packaging of beverages. In this case a beverage container is formed from a shaped pre-form by blow moulding, then the container is filled with a sterile drink and finally the filled container is filled with a sterilized closure cap. In this case different degrees of sterilization are controlled in various parts of the chamber, the degrees of sterilization being correlated with the degree which is necessary for the method step that is being carried out in the part of the chamber in question.

In this production method the entire production process of the bottle and also the filling and closure process are carried out in a continuous manner under sterile conditions. In this case a complete shaping unit of the containers is arranged in a clean room. This method ensures a high degree of sterilization and cleanness of the containers filled in this way. On the other hand, however, the outlay for the sterilization is relatively high since on the one hand very large rooms have to be kept sterile and on the other hand a plurality of machine parts are also present, namely in the region of the blow-moulding apparatus, which have to be kept sterile.

The object of the present invention is therefore to reduce the outlay for the sterilization or keeping sterile of a shaping unit or blow-moulding device for containers. Conversely, however, production conditions which are as sterile as possible should be provided for the containers. This is attained according to the invention by an apparatus according to claim 1 and a method according to claim 15. Advantageous embodiments and further developments form the subject matter of the sub-claims.

An apparatus according to the invention for shaping plastics-material pre-forms to form plastics-material containers has a conveying device on which a plurality of blow-moulding stations are arranged, each of these blow-moulding stations having a blow mould inside which a plastics-material pre-form is capable of being shaped to form a plastics-material container, and the apparatus having a clean room inside which the containers can be conveyed. According to the invention that region of the conveying device on which the blow-moulding stations are arranged is arranged in the clean room. Preferably a further region of the conveying device is arranged outside the clean room.

In this way, in particular in the case of the apparatus according to the invention, a clean room channel is provided through which the plastics-material pre-forms or containers are conveyed in the blow-moulding stations and a further region of the conveying device is moved outside the clean room. In this way, parts of the shaping unit such as a blow-moulding machine, for example the entire blow-moulding wheel or the blow-moulding cavities are separated from the remainder of the blow-moulding machine by a clean room or closed-off isolator.

It is preferable for the conveying device to be a conveying wheel which rotates about a pre-set axle, in which case at least the axle or a shaft of the conveying device is arranged outside the clean room. This ensures that the clean room is kept as small as possible and so the internal volume of the clean room can be kept small. In addition, it is also made possible in this way that as large a number of machine parts as possible, which are not in direct contact with the blow-moulding stations, can be guided outside the clean room, and in this way contamination can also be kept low.

It is preferable for the clean room to have an annular profile or a toroidal profile at least in part, in which case, however, the cross-section of this toroidal profile preferably deviates from a circular shape. This means that the blow-moulding stations are guided by the conveying device on a substantially circular path.

In the case of a further advantageous embodiment a stretch rod for stretching the plastics-material pre-forms is arranged at each blow-moulding station, and this stretch rod projects at least temporarily and in part out of the clean room. As is known, a stretch rod is used in order to extend the plastics-material pre-forms in the framework of the production process. In principle it would also be possible for the entire stretch rod always to be guided in the interior of the clean room. For this purpose, however, the clean room would have to be enlarged in its volume to a considerable extent. In the preferred embodiment it is therefore proposed that the stretch rod should project outwards through an opening in the clean room. In order to prevent contamination of this stretch rod at the same time, it is particularly preferred for a folding bellows to be provided, in the interior of which the stretch rod extends, so that the stretch rod itself does not come into contact with the outside. In this way, sterile conditions also prevail inside the folding bellows.

It is preferable for the clean room to be bounded by a plurality of walls and for at least one of these walls to be movable, and in particular rotatable, with respect to a further wall.

It is preferable for a wall of the clean room arranged radially on the outside to be arranged in a stationary manner. In this way a wall with an external profile, in particular cylindrical, can be provided, which wall bounds the clean room. A further wall, which bounds the clean room with respect to the other side and which is arranged in a rotatable manner, is provided by the interior of this wall. It is preferable for this wall arranged on the inside to be jointly rotated with the individual blow-moulding stations. It is preferable for the rotatable wall mentioned and the wall arranged in a stationary manner to be opposite each other. In addition, the clean room is bounded by a wall in the form of a cover, this cover preferably being formed integrally in one piece with the rotatable wall.

It is preferable for a sealing device to be arranged between at least two wall[s] or a wall and a cover. This sealing device preferably seals off from one another parts which are movable with respect to one another. In this way it would be possible, for example, for a wall and a cover to have provided between them a so-called surge chamber in which a water duct—preferably annular in this case—is provided in which a portion of the part movable with respect to this water duct is guided.

In the case of a further advantageous embodiment the apparatus has a supply device in order to pass the plastics-material pre-forms on to the conveying device, and this supply device is arranged inside the clean room. In this case the clean room thus preferably has a hollow or a recess out of the otherwise circular cross-section, and the supply device such as for example a conveying star for the pre-forms is arranged in this hollow in a corresponding manner. In this way, a continuous transfer of the containers from the supply device to the conveying device can take place inside a sterile room.

In the case of a further advantageous embodiment the apparatus also has a removal device in order to take up the containers produced from the conveying device, and this removal device is likewise arranged inside the clean room. In this way it is possible for a clean room to be maintained, even during the removal of the containers. It is thus possible for the introduction of pre-forms into the isolator or clean room from units arranged in front and for the removal of the bottles to a following unit under clean-room conditions to be possible. The isolator or clean room can be acted upon with cleaning and sterilization agents.

In the case of a further advantageous embodiment a sterile gas is provided inside the clean room and this sterile gas is under a pressure which is higher than a pressure outside the clean room. In this way it is optionally possible, by the introduction of sterilized air, for the clean room to be kept at a higher pressure level than the outside, as a result of which the penetration of micro-organisms can be prevented. In addition, it is possible for an antimicrobial active substance to be continuously supplied to the clean room and for a hygienic environment to be maintained in this way.

By means of a spatially bounded clean room in the blow-moulding device it is possible for previously sterilized pre-forms to be conveyed to the filling means without re-contamination both on the outside and on the inside during the stretch blow-moulding procedure. In addition, the clean room is simpler to keep to a level low in germs as compared with the shaping apparatus as a whole.

The present invention additionally relates to a plant for producing plastics-material containers, which comprises an apparatus for shaping plastics-material containers of the type described above, as well as a heating device, this heating device being arranged upstream with respect to the apparatus mentioned above in a conveying direction of the plastics-material pre-forms. This heating device is used to warm the pre-forms so that they can then be expanded to form containers in a blow-moulding process. A filling device, which fills the containers with a beverage, in particular with an aseptic product, is provided downstream or after the shaping apparatus. In this case this filling device is also arranged in a clean room. In addition, the clean room preferably extends into the region of a closure device which closes the containers with a closure.

In addition, the plant preferably has a sterilization device which sterilizes at least one region of the plastics-material pre-forms before they reach the apparatus. In this case this sterilization can be carried out with a gaseous medium, such as in particular hydrogen peroxide. It would also be possible, however, for the sterilization to be carried out by using radiation, such as for example electron beams and/or UV light. In this case it is preferable for a sterilization device to be provided which in particular also sterilizes the internal surface of the plastics-material pre-forms. In addition, it is also possible, however, for the external surface of the plastics-material pre-forms to be sterilized.

In the case of a further advantageous embodiment the plant has a further clean room which is arranged in front of the apparatus mentioned above in the conveying direction of the plastics-material pre-forms. It is preferable for this further clean room to merge into the clean room of the shaping apparatus. In this way it is possible for the plastics-material containers, starting from their sterilization, to be conveyed in a continuous manner until they are closed and nevertheless for the clean rooms required for this to be kept relatively small. It is thus preferable for the clean room to be provided in the form of a channel which extends from the sterilization device as far as the closure device and which in a particularly preferred manner is adapted in each case to the corresponding blow-moulding stations or holding devices such as gripping elements for the pre-forms or plastics-material containers.

The present invention additionally relates to a method of shaping plastics-material pre-forms to form plastics-material containers, in which the plastics-material pre-forms are conveyed by means of a conveying device, on which a plurality of blow-moulding stations are arranged, and are shaped to form plastics-material containers during this conveying. In this case the blow-moulding stations are conveyed at least in part and preferably in their entirety through a clean room. According to the invention at least one region of the conveying device is arranged outside the clean room. Expressed in more precise terms, it is preferable for at least one region of the conveying device also to be moved outside the clean room. In the case of a further preferred method the blow-moulding stations are moved on a circular path and it is particularly preferred for them to be moved in a continuous manner inside the clean room.

Further advantages and embodiments may be seen in the accompanying drawings. In the drawings FIG. 1 is a diagrammatic illustration of a plant for producing plastics-material containers, and FIG. 2 is a view of a clean room in the region of a blow-moulding station.

FIG. 1 is a diagrammatic illustration of a plant for producing plastics-material containers. This plant 50 has a heating device 30 in which plastics-material pre-forms 10 are heated. In this case these plastics-material pre-forms 10 are guided through this heating device 30 by means of a conveying device 34, such as in this case a circulating chain, and in this case are heated with a plurality of heating elements 31. A transfer unit 36, which transfers the pre-forms 10 to a sterilization device 32, is attached to this heating device 30. In this case this sterilization device 32 likewise has a conveying wheel 37, and sterilization elements can be arranged on this conveying wheel 37 or in a stationary manner. In this region for example, sterilization by hydrogen peroxide gas or even, as mentioned above, by electromagnetic radiation is possible. In particular, internal sterilization of the pre-forms is carried out in this region.

The reference number 6 designates in its entirety a clean room, the outer boundaries of which are indicated here by the dotted line L. It is evident that this clean room 6 starts in the region of the sterilization device 32. It is possible for lock devices to be provided in this region in order to introduce the plastics-material pre-forms into the clean room 6, without an excessive amount of gas being lost inside the clean room.

The clean room is, as indicated by the broken line L, adapted to the external shape of the individual components of the plant. In this way the volume of the clean room can be reduced.

The reference number 1 designates in its entirety a shaping apparatus in which a plurality of blow-moulding stations 8 are arranged on a conveying wheel 2, only one of the blow-moulding stations 8 being illustrated in this case. The plastics-material pre-forms 10 are expanded by these blow-moulding stations 8 to form containers 20. Although not shown in detail here, the entire region of the conveying device 2 is not situated inside the clean room 6, but rather the clean room 6 or isolator is designed to a certain extent in the form of a mini-isolator inside the apparatus as a whole. In this way, it would be possible for the clean room to be designed in the manner of a channel, at least in the region of the shaping apparatus 1.

The reference number 22 designates a supply device which transfers the pre-forms to the shaping apparatus 1, and the reference number 24 designates a removal device which removes the plastics-material containers 20 produced from the shaping apparatus 1. It is evident that in the region of the supply device 22 and the removal device 24 the clean room 6 has recesses in each case which receive these devices 22, 24. In this way a transfer of the plastics-material pre-forms 10 to the shaping apparatus 1 or a taking-on of the plastics-material containers 20 from the shaping apparatus 1 respectively can be carried out in a particularly advantageous manner.

The expanded plastics-material containers are transferred by a transfer unit 42 to a filling device 40 and are then removed from this filling device 40 by way of a further conveying unit 44. In this case the filling device 40 is also situated inside the aforesaid clean room 6. In the case of the filling device it would also be possible for the entire filling device 40 with for example a reservoir for a beverage not to be arranged completely inside the clean room 6, but in this case too only those regions in which the containers are in fact guided. In this respect it would also be possible for the filling device to be designed in a manner similar to the apparatus 1 for shaping plastics-material pre-forms 10.

As mentioned, the clean room 6 is reduced in the region of the apparatus 1 to as small an area as possible, namely substantially to the blow-moulding stations 8 themselves. As a result of this compact design of the clean room 6 it is possible, in an easier and more rapid manner, to produce a clean room altogether and even keeping sterile in the operating phase is less complicated. In addition, less sterile air is required, which leads to smaller filter plants, and the risk of uncontrolled swirl formation is also reduced.

FIG. 2 is a detailed illustration of the apparatus 1 in the region of a blow-moulding station 8. A plurality of blow-moulding stations 8 of this type is moved in a manner rotating about an axis X by a conveying device 2. The blow-moulding station 8 is, as may be seen from FIG. 2, guided inside the clean room 6 which in this case is designed in the manner of a channel. This clean room 6 is closed off by a movable lateral wall 16 and a cover 17 formed in one piece with this lateral wall 16. In this case this lateral wall 16 and the cover 17 turn jointly with the blow-moulding station 8.

The reference number 18 designates a further wall which bounds the clean room 6. In this case this wall 18 is a wall situated on the outside which is arranged stationary. The cover 17 and the wall 18 have provided between them a sealing device 25, which seals off from each other the elements 17 and 18 which are movable with respect to each other, for example, as mentioned above, whilst using a surge chamber. The lower region of the wall 18 is arranged on a base 13 in a fixed and sealed-off manner. A support 26, which likewise moves in a turning manner and on which in turn a holding device 23 is provided which holds the blow-moulding station 8, is provided inside the clean room 6 and resting against the wall 16 in this case.

The reference number 11 designates a follower device which can be actuated by a guide curve 9 in order to open and close the blow-moulding station on its path through the clean room 6, in order to insert in particular the plastics-material pre-form into the blow-moulding station and in order also to remove it again. In this case a guide curve 9 is also arranged inside the clean room 6. It would also, however, be possible for example for just a portion 19 to extend out of the clean room 6 below the individual blow-moulding stations 8.

The conveying device 2 can also have further elements which are arranged above the clean room 6.

In this case the support 26 is arranged in a fixed manner on a holding body 29 and this holding body in turn is movable with respect to the base 13. In this case the reference number 27 designates a further sealing device which in this region too seals the regions 13 and 29 which are movable with respect to each other.

The reference number 5 designates a stretch rod which is movable with respect to the blow-moulding station in order to stretch the plastics-material pre-forms 10 in the longitudinal direction thereof. In this case the cover 17 has arranged on it a slide 12, opposite which the stretch rod is movable in the direction Y. The reference number 14 designates a further holding means for this slide 12 of the stretch rod 5.

It is evident that specified areas of the stretch rod are both outside the clean room 6 and inside the clean room during the blow-moulding procedure. For this purpose it is possible for a protective device 4 such as a folding bellows, which surrounds the stretch rod 5 so that no area of the stretch rod 5 comes directly into contact with the outside environment, to be provided outside the clean room 6 and above the slide 12.

All the features disclosed in the application documents are claimed as being essential to the invention, insofar as they are novel either individually or in combination as compared with the prior art.

The invention claimed is:

1. An apparatus for shaping plastics-material pre-forms to form plastics-material containers with a conveying device on which a plurality of blow-moulding stations are arranged, wherein each of these blow-moulding stations has a blow mould inside which a plastics-material pre-form is capable of being shaped to form a plastics-material container, wherein the apparatus has a clean room inside which the plastics-material pre-forms can be conveyed, wherein the region of the conveying device on which the blow-moulding stations are arranged in the clean room and at least one further region of the conveying device is arranged outside the clean room, wherein the conveying device has a conveying wheel which rotates about a pre-set axle of the conveying device, wherein at least the axle of the conveying device is arranged at the at least one further region outside the clean room, and wherein the clean room has an annular profile at least in part so as to guide the blow-moulding stations and the containers to be or having been blown along a substantially circular path within the clean room.

2. An apparatus according to claim 1, wherein a stretch rod for stretching the plastics-material pre-forms is arranged at each blow-moulding station, and this stretch rod projects at least temporarily and in part out of the clean room, wherein this projecting portion of the stretch rod is surrounded by a protective device.

3. An apparatus according to claim 1, wherein the clean room is bounded by a plurality of walls and at least one of these walls is arranged so as to be rotatable with respect to a further wall.

4. An apparatus according to claim 3, wherein a wall of the clean room arranged radially on the outside is arranged in a stationary manner.

5. An apparatus according to claim 3, wherein a wall of the clean room arranged radially on the inside is movable.

6. An apparatus according to claim 3, wherein a sealing device is arranged between at least two walls.

7. An apparatus according to claim 1, wherein the apparatus has a supply device in order to pass the plastics-material pre-forms on to the conveying device, and this supply device is arranged inside the clean room.

8. An apparatus according to claim 1, wherein the apparatus has a removal device in order to take up the plastics-material containers from the conveying device, and this removal device is arranged inside the clean room.

9. An apparatus according to claim 1, wherein a sterile gas is provided inside the clean room and this sterile gas is under a pressure which is higher than a pressure outside the clean room.

10. A plant for producing plastics-material containers with an apparatus according to claim 1 and with a heating device, wherein this heating device is arranged upstream with respect to the apparatus in a conveying direction of the plastics-material pre-forms.

11. A plant according to claim 10, wherein the plant has a sterilization device which sterilizes at least one region of the plastics-material pre-forms before they reach the apparatus.

12. A plant according to claim 10, wherein the plant has a further clean room which is arranged in front of the apparatus in the conveying direction of the plastics-material pre-forms.

13. An apparatus according to claim 1, wherein further comprising a sterilization device arranged apart from the circular path.

14. An apparatus according to claim 1, wherein one and only one blow mould type is transported and arranged along the circular path.

* * * * *